US009103769B2

(12) United States Patent
Duden

(10) Patent No.: US 9,103,769 B2
(45) Date of Patent: Aug. 11, 2015

(54) APPARATUS AND METHODS FOR CONTROLLING ELECTRON MICROSCOPE STAGES

(75) Inventor: Thomas Duden, Bielefeld (DE)

(73) Assignee: The Regents of the University of California, Oakland, CA (US)

( * ) Notice: Subject to any disclaimer, the term of this patent is extended or adjusted under 35 U.S.C. 154(b) by 1275 days.

(21) Appl. No.: 12/968,024

(22) Filed: Dec. 14, 2010

(65) Prior Publication Data

US 2011/0174972 A1 Jul. 21, 2011

Related U.S. Application Data

(60) Provisional application No. 61/286,667, filed on Dec. 15, 2009.

(51) Int. Cl.
G01N 23/205 (2006.01)
H01J 37/20 (2006.01)
G01N 23/203 (2006.01)

(52) U.S. Cl.
CPC ............ *G01N 23/205* (2013.01); *G01N 23/203* (2013.01); *H01J 37/20* (2013.01); *H01J 2237/20285* (2013.01)

(58) Field of Classification Search
CPC ............ G01N 23/20; G01N 23/20008; G01N 23/20058; G01N 23/02; G01N 23/20075; G01N 23/205; H01J 37/26; H01J 37/261; H01J 37/20; H01J 2237/20285; H01J 2237/202
See application file for complete search history.

(56) References Cited

U.S. PATENT DOCUMENTS 4,429,307 A 1/1984 Fortescue
5,179,280 A * 1/1993 Wang ............................ 250/311
5,479,191 A 12/1995 Komatsu (Continued)

FOREIGN PATENT DOCUMENTS

EP 1058095 12/2000
JP 08-327310 12/1996

OTHER PUBLICATIONS

Engineeringtalk, The Engineer, Products and services for engineers, "Absolute rotary position sensing with zero wear, a RDP Electronics product story," Engineeringtalk editorial team, Feb. 17, 2000.
Manning, Bryan et al., "A high-precision noncontact electronic gap measurement gauge," Capacitec, 2002.
"Capacitec CMS-3™, Capacitive Measurement System for hole diameter measurement," 2005.

(Continued)

Primary Examiner — Jack Berman
(74) Attorney, Agent, or Firm — Lawrence Berkeley National Laboratory

(57) ABSTRACT

Methods and apparatus for generating an image of a specimen with a microscope (e.g., TEM) are disclosed. In one aspect, the microscope may generally include a beam generator, a stage, a detector, and an image generator. A plurality of crystal parameters, which describe a plurality of properties of a crystal sample, are received. In a display associated with the microscope, an interactive control sphere based at least in part on the received crystal parameters and that is rotatable by a user to different sphere orientations is presented. The sphere includes a plurality of stage coordinates that correspond to a plurality of positions of the stage and a plurality of crystallographic pole coordinates that correspond to a plurality of polar orientations of the crystal sample. Movement of the sphere causes movement of the stage, wherein the stage coordinates move in conjunction with the crystallographic coordinates represented by pole positions so as to show a relationship between stage positions and the pole positions.

28 Claims, 8 Drawing Sheets

(56) References Cited

U.S. PATENT DOCUMENTS

| | | |
|---|---|---|
| 5,736,865 A | 4/1998 | Nelson et al. |
| 5,872,408 A | 2/1999 | Rakov |
| 6,388,262 B1 | 5/2002 | Alani et al. |
| 6,492,911 B1 | 12/2002 | Netzer |
| 7,342,226 B2 * | 3/2008 | Soeda .......................... 250/311 |
| 8,008,621 B2 * | 8/2011 | Jeong et al. .................. 250/307 |
| 2003/0042409 A1 | 3/2003 | Warren et al. |
| 2004/0041572 A1 | 3/2004 | Lin et al. |
| 2007/0180924 A1 | 8/2007 | Warren et al. |
| 2011/0175629 A1 | 7/2011 | Duden |

OTHER PUBLICATIONS

"Capacitec Non-contact displacement standard products," 1998.
AZoNanotechnology, "Queensgate Instruments," Dec. 9, 2005.
PI Piezo—Nano—Positioning, "Capacitive displacement sensors—nanometrology Solutions," Jun. 2007.
WO patent application No. PCT/US2009/051988, International Search Report and Written Opinion mailed Feb. 1, 2010.
EP patent application No. 09805368.9, Extended European Search Report mailed Dec. 20, 2011.
U.S. Appl. No. 13/002,762, Office Action mailed Jun. 18, 2013.

* cited by examiner

US 9,103,769 B2

APPARATUS AND METHODS FOR CONTROLLING ELECTRON MICROSCOPE STAGES

CROSS REFERENCE TO RELATED PATENT APPLICATION

This application claims priority under 35 U.S.C. §119 of U.S. Provisional Patent Application No. 61/286,667 filed 15 Dec. 2009 by Thomas Duden, which application is incorporated herein by reference in its entirety for all purposes.

STATEMENT OF GOVERNMENT RIGHTS

This invention was made with government support under Contract No. DE-AC02-05CH11231 awarded by the U.S. Department of Energy. The government has certain rights in the invention.

BACKGROUND OF THE INVENTION

The present invention relates generally to electron microscopy for imaging samples, and more specifically to apparatus and methods for imaging crystalline structures.

Since electron microscopes generally utilize the small de Broglie wavelength of electrons, electron microscopes can image at significantly higher resolutions than light microscopes. One application of electron microscopy enables examination of relatively tiny structures of a specimen, such as a single column of atoms or the crystalline structure of a material.

An operator of an electron microscope may encounter several challenges when attempting to image a crystalline structure at high resolutions, e.g., so as to resolve individual atoms. For example, unless the atoms of such a crystalline structure are perfectly aligned relative to the viewing axis so that the atoms in each column that is parallel to such axis are aligned, any misaligned atoms will tend to blur together so that the individual atoms cannot be precisely imaged with clarity. The operator typically repeatedly, manually tilts the sample until the atomic columns are perfectly aligned in a particular polar orientation. Additionally, once the sample is tilted precisely so as to image at a first polar orientation, the operator will often need to again repeatedly tilt the sample so as to image the sample at a different polar orientation. The operator typically manually performs numerous and time consuming tilt adjustments at each different polar orientation so as to achieve a clear image at such different polar orientations.

The efficiency of such manual alignment techniques is highly dependent on the particular expertise of the operator and, additionally, these manual alignment processes tend to be very tedious for the operator. Accordingly, improved mechanisms and techniques for facilitating the imaging of crystalline structures would be beneficial.

SUMMARY OF THE INVENTION

In one embodiment, a method of generating an image (or diffraction patterns) of a specimen with a microscope (e.g., electron or X ray microscopy) is disclosed. In one aspect, the microscope may include a beam generator for directing an incident beam towards a crystal sample, a stage for holding and moving the crystal sample, a detector for detecting beams that are scattered from the crystal sample in response to the incident beam, and an image generator for generating an image or diffraction patterns of the crystal sample from the scattered beams. A plurality of crystal parameters, which describe a plurality of properties of the crystal sample, are received. In a display associated with the microscope, an interactive control sphere based at least in part on the received crystal parameters and having the same rotational constraints that the microscope sample stage has and that is rotatable by a user to different sphere orientations is presented. The sphere includes a plurality of stage coordinates that correspond to a plurality of positions of the stage and a plurality of pole coordinates that correspond to a plurality of pole positions of the crystal sample. Movement of the sphere causes movement of the stage, wherein the stage coordinates move in conjunction with the crystallographic coordinates represented by the crystallographic poles so as to show a relationship between stage positions and the crystallographic pole positions.

In a specific implementation, the stage and crystallographic coordinates of the control sphere are automatically synchronized based on a user alignment process. After synchronizing the stage and crystallographic coordinates of the control sphere and when a specific pole position is selected, the stage, along with the presented control sphere, can then be automatically moved to the selected specific pole position. In a further aspect, presenting the interactive sphere is also based on simulating a simulated diffraction pattern based at least, in part, on the received crystal parameters. In this aspect, in a display associated with the microscope, an actual diffraction pattern obtained from imaging the crystal sample is presented, and selection of a center or a plurality of diffraction points of the actual diffraction pattern for geometrically determining the center are received. A tilt angle relationship between the stage and pole positions may then be automatically determined based on the selection of the center or the plurality of diffraction points of the actual diffraction pattern. For example, selection comprises selection of the center or selection of three non-colinear diffraction points for each of either two Laue zones or a same Laue zone of the actual diffraction pattern. In another example, the actual diffraction pattern is in the form of a Kikuchi line pattern acquired at two different tilt angles. In another example, user selection comprises selection of the center or selection of the crossover points of the Kikuchi line pattern.

In a further embodiment, the user alignment process further comprises (i) in the display, presenting an overlay of the simulated diffraction pattern and the actual diffraction pattern, (ii) receiving an adjustment of a rotation position of the crystallographic coordinates with respect to the actual diffraction pattern, wherein the adjustment is accomplished by rotating the simulated diffraction pattern with respect to the actual diffraction pattern to thereby cause alignment of a plurality of crystallographic model coordinates with a plurality of actual crystallographic sample coordinates, (iii) determining a rotation angle relationship between the stage and pole positions based on the received adjustment, (iv) in the display, presenting the actual diffraction pattern and its plurality of different intensity values of diffraction points, (v) receiving a selection of a center and a plurality of non-colinear points of the actual diffraction pattern, and (vi) automatically adjusting the determined rotation relationship based on a center of mass calculation of the different intensity values with respect to the center of the actual diffraction pattern and non-colinear points so as to align the stage and pole positions of the control sphere to thereby accurately correspond with the stage and pole positions of the crystal sample.

In another embodiment, the invention pertains to a microscope (e.g., TEM) that comprises a beam generator for directing an incident beam towards a crystal sample, a stage for holding and moving the crystal sample, a detector for detecting beams that are scattered from the crystal sample in response to the incident beam, an image generator for generating an image of the crystal sample from the scattered beams, and a controller that is operable to perform at least some of the above described method operations. In another embodiment, the invention pertains to at least one computer readable storage medium having computer program instructions stored thereon that are arranged for performing at least some of the above described method operations.

These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE SPECIFIC EMBODIMENTS

Reference will now be made in detail to the specific embodiments of the invention. Examples of these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order to not unnecessarily obscure the present invention.

Certain embodiments of the present invention provide mechanisms for facilitating alignment of a crystal at a polar orientation with respect to a microscope, such as a transmission electron microscope (TEM). Although embodiments of the present invention are described herein as being applied to a TEM system, the techniques may be applied to other types of systems for obtaining images or diffraction patterns from a sample, such as any type of imaging or diffractive imaging type systems (e.g., an electron or x-ray microscope).

Figure 1:
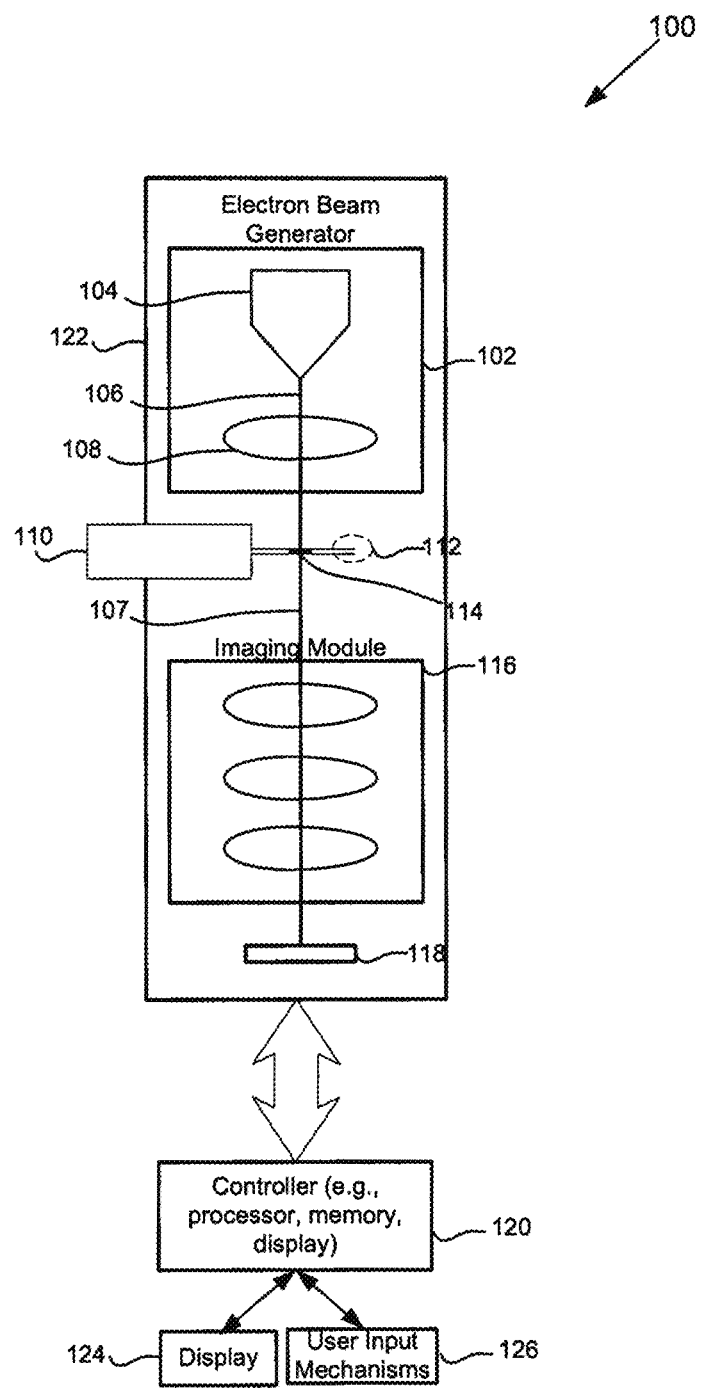
FIG. 1 is a diagrammatic representation of an example transmission electron microscope (TEM) system in which techniques of the present invention may be implemented in accordance with one embodiment.

Prior to describing detailed mechanisms for facilitating crystal alignment, a system will first be briefly described to provide an example context for practicing techniques of the present invention. FIG. 1 is a diagrammatic representation of an example transmission electron microscope (TEM) system 100 in which techniques of the present invention may be implemented in accordance with one embodiment. As shown, the TEM system 100 includes an electron beam generator 102 for emitting and directing an electron beam 106 towards a sample 114, a sample stage 110 for holding and moving the sample with respect to the electron beam 106, an imaging (or diffractive imaging) module 116 for directing output electron beams 107 scattered from the sample 114, and towards screen 118 for imaging (or providing diffraction patterns for) the output beams from the sample. The TEM system 100 also includes a vacuum chamber 122 for holding the various components or portions of such components for illuminating and imaging a sample within a vacuum.

In general, lenses of variable focusing power and deflecting direction are formed by generating and manipulating magnetic fields to focus and/or deflect the beam in various directions. For example, an electrostatic lens may be formed from one or more electrodes. Each electrode has a hole around which field lines are generated that produce a focusing effect and converges the electron beam into a particular cross-over or focal point. The field line's strength and resulting position of the cross-over point depend on the value of the voltage. Additionally, coupling of two deflectors in opposite directions with a small intermediate gap allows for the formation of a shift in the beam path. Lens shaping may also be achieved based on distribution of magnetic flux.

The electron beam generator 102 may be arranged in any suitable configuration for generating an incident electron beam 106 that will result in electrons being transmitted and scattered through the specimen 114. As shown, the electron beam generator includes an emission source 104, such as a tungsten filament or a lanthanum hexaboride (LaB$_6$) source or a field emitting tip which could be cold or heated, that can be connected to a high voltage source (e.g., 20-300 kV) so as to excite and emit electrons from the filament or source by a thermionic or field electron emission process into the vacuum chamber 122. The electron beam generator 102 may also include any suitable number and type of illumination components 108 for extracting and directing the electrons towards the sample 114. Example components may include a Wehnelt cylinder for serving as an anode for extracting electrons from the electron source 104, lenses for formation of the electron beam to the desired size and location, an aperture, and an objective lens for focusing the beam onto the sample. The aperture forms a hole through which the beam (or a portion of the beam) is directed. The beam current density depends on the relative placement of the cross-over point with respect to the aperture. For example, if the cross-over point is located at the aperture, the beam current density is maximized. By selecting a particular gun lens voltage, a particular cross-over point with respect to the aperture is selected, which results in a particular beam current density value. A suppressor may be also used to inhibit spurious electrons that deviate from a direct path to the specimen 112. For example, the suppressor may include a hole around which a negative potential is generated to repel the electrons to follow a trajectory that is substantially through a center of the hole.

The imaging module 116 may be configured with any suitable components for directing output electrons onto screen or detector 118. For example, the imaging module may include an objective lens for focusing and changing magnification of the output beam, and projector lenses for expanding the output beam onto the screen or display. The detector 118 may take any suitable form for detecting and imaging (or obtaining diffraction patterns from) scattered electrons, such as a fluorescent or phosphor screen and/or CCD (charged couple device) or any type of camera or image sensor. After the electrons impinge on the detector 118, an image (or diffraction patterns) may be formed from the detected signal.

The TEM system may also include a controller 120, e.g., a computer system, which may be configured to control the various components of the TEM system, as well as processing the detected signal to form various images, such as a real image of the crystal and/or a diffraction pattern or a Kikuchi line image of the crystal. The controller 120 may also be coupled to various user input mechanisms 126, such as a joystick, trackball, trackpad, keyboard, mouse, etc., for receiving user input and coupling with one or more display (e.g., 124) for displaying various user interfaces and data, such as real and diffraction images.

Embodiments of the present invention may also be practiced in a wide variety of network environments including, for example, TCP/IP-based networks (e.g., Rate Control Protocol or RCP, Transport Control Protocol or TCP, Fast TCP, Stream-based TCP/IP or STCP, eXplicit Control Protocol or XCP, etc.), telecommunications networks, wireless networks, etc. In addition, the computer program instructions with which embodiments of the invention are implemented may be stored in any type of computer-readable media, and may be executed according to a variety of computing models including a client/server model, a peer-to-peer model, on a standalone computing device, or according to a distributed computing model in which various of the functionalities described herein may be effected or employed at different locations.

Regardless of the system's configuration, it may employ one or more memories or memory modules configured to store data, program instructions for the operations and/or the inventive techniques described herein. The program instructions may control the operation of an operating system and/or one or more applications, for example. The memory or memories may also be configured to store crystal parameters, crystal models, coordinates, detected signals, images, etc.

Because such information and program instructions may be employed to implement the systems/methods described herein, the present invention relates to tangible machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

The TEM includes any suitable movement mechanism for tilting and moving the specimen relative to the incident beam. For instance, the movement mechanism may take the form of a tilt-rotation or a double-tilt stage. In the illustrated example, the movement mechanism is in the form of a tilt-rotation type stage, which includes an alpha stage 110 and a gamma stage 112 in the form of two wires between which the specimen 114 is placed. The stage is typically configured to insert the sample 114 into the vacuum chamber 122 without damaging or misaligning the optics of the TEM system 100. In a crystallography application, the stage is typically sized to holding a relative small crystal, e.g., between about 1-3 mm.

Figure 2A:
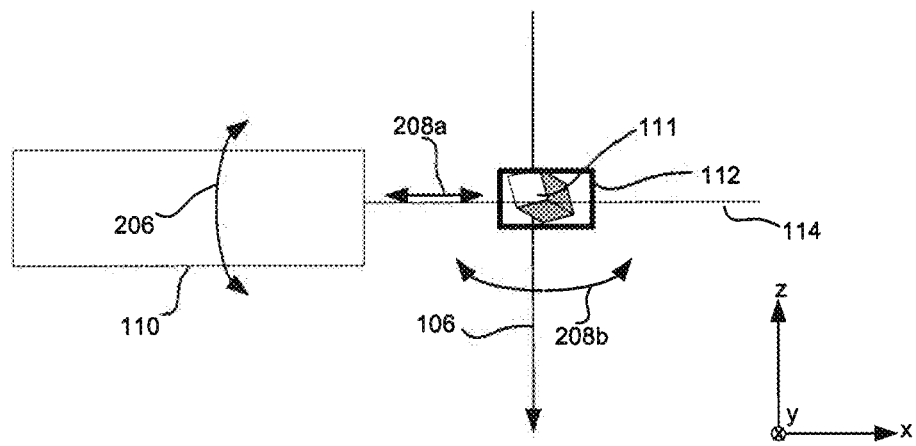
FIG. 2A is a diagrammatic representation of one implementation of a tilt-rotation stage shown in a side view perspective.

In general, the movement mechanism or stage 110 is controllable to move the sample with respect to the incident beam. Such movement may be achieved by way of examples include stepper motors, piezoelectric motors, etc, which can be receive computer based stage input. FIG. 2A is a diagrammatic representation of one implementation of a tilt-rotation stage shown in a side view perspective. As shown, the y axis goes into the page and the incident beam 106 is directed along the z axis. The gamma stage may include wires 114 between which the sample 112 is held. The wires 114 are coupled with the alpha stage 110.

Figure 2B:
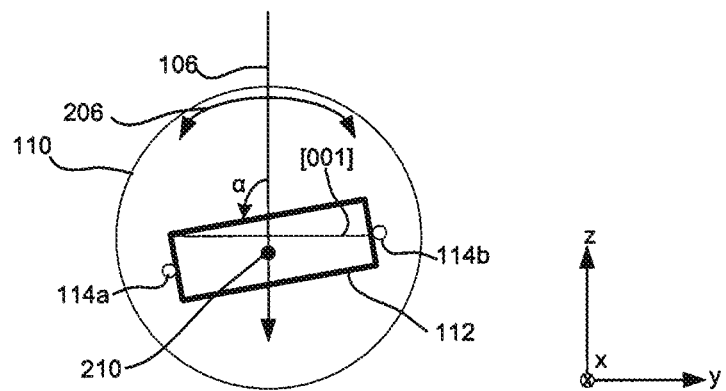
FIG. 2B illustrates movement of the alpha stage of a tilt-rotation movement mechanism from a view perspective that is orthogonal to the yz plane.

The alpha stage can generally be operable to move in the z or y directions, as well as tilt the sample in direction 206 within the yz plane. FIG. 2B illustrates movement of the alpha stage 110 of a tilt-rotation movement mechanism from a view perspective that is orthogonal to the yz plane. As shown, the alpha stage 110 is operable to tilt the sample 112 around the x axis 210 in direction 206 to achieve angle α. The alpha stage 110 may be controlled to tilt the sample so as to align, for example, polar plane [001] orthogonal to the incident beam 106 (as shown).

Figure 2C:
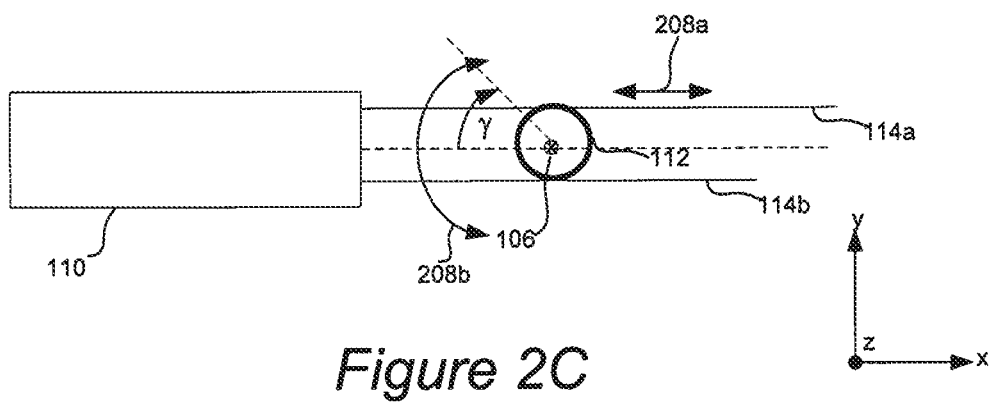
FIG. 2C illustrates movement of the gamma stage of a tilt-rotation movement mechanism from a view that is orthogonal to the xy plane

The wires (e.g., 114a and 114b) of the gamma stage are generally operable to move in and out so as to cause movement in direction 208a (e.g., along the x axis), as well as rotation in direction 208b (in the xy plane) as illustrated in FIG. 2C, which shows a view that is orthogonal to the xy plane. The x direction 208a movement may be achieved by moving the wires or pins in and out together at the same rate, while a γ angle may be achieved from the pins 114a and 144b going in and out individually at different rates. For example, wire 114b may be moved in the −x direction, while wire 114a remains still to thereby rotate the sample in a clockwise direction around the z axis.

Certain embodiments of the present invention facilitate alignment of a specified polar plane of the crystal so that such polar plane is orthogonal to the incident beam 106. In general, the orientation of the crystal's polar planes with respect to the orientation of stage positions, as well as corresponding microscope or display coordinates, is not accurately known upon loading of the sample. For instance as shown, the orientation of the crystal structure 111 (e.g., FIG. 2A) with respect to the sample 112 or stage position (as well as the microscopy's display coordinates) is not accurately known. In one implementation, offsets between such various orientations are determined based on a simplified user alignment process so that the stage can be automatically moved to selected crystal orientations without further (or with minimal) manual stage adjustments by the operator.

Figure 3:
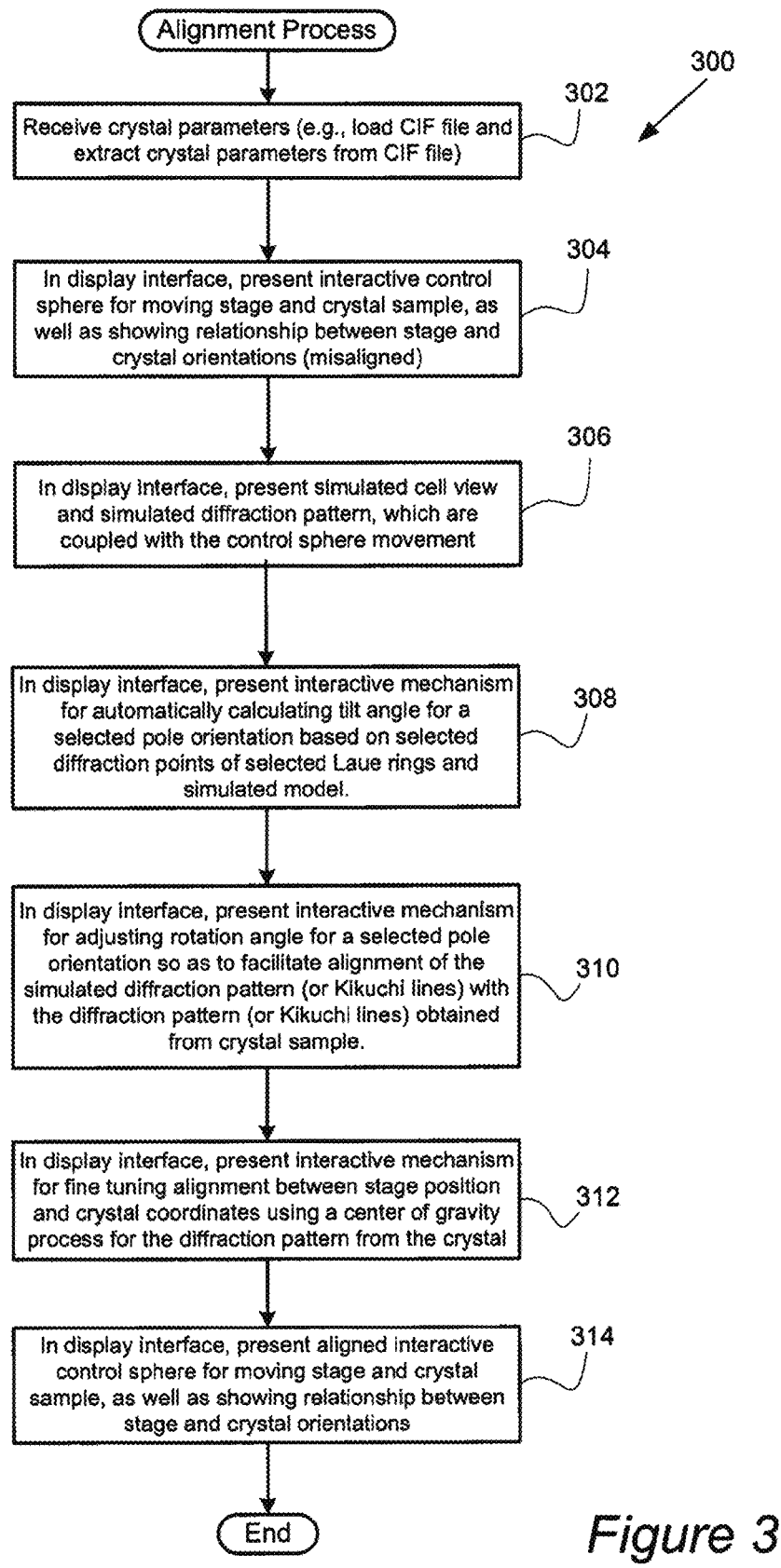
FIG. 3 is a flow chart illustrating an alignment procedure in accordance with one embodiment of the present invention.
Figure 4A:
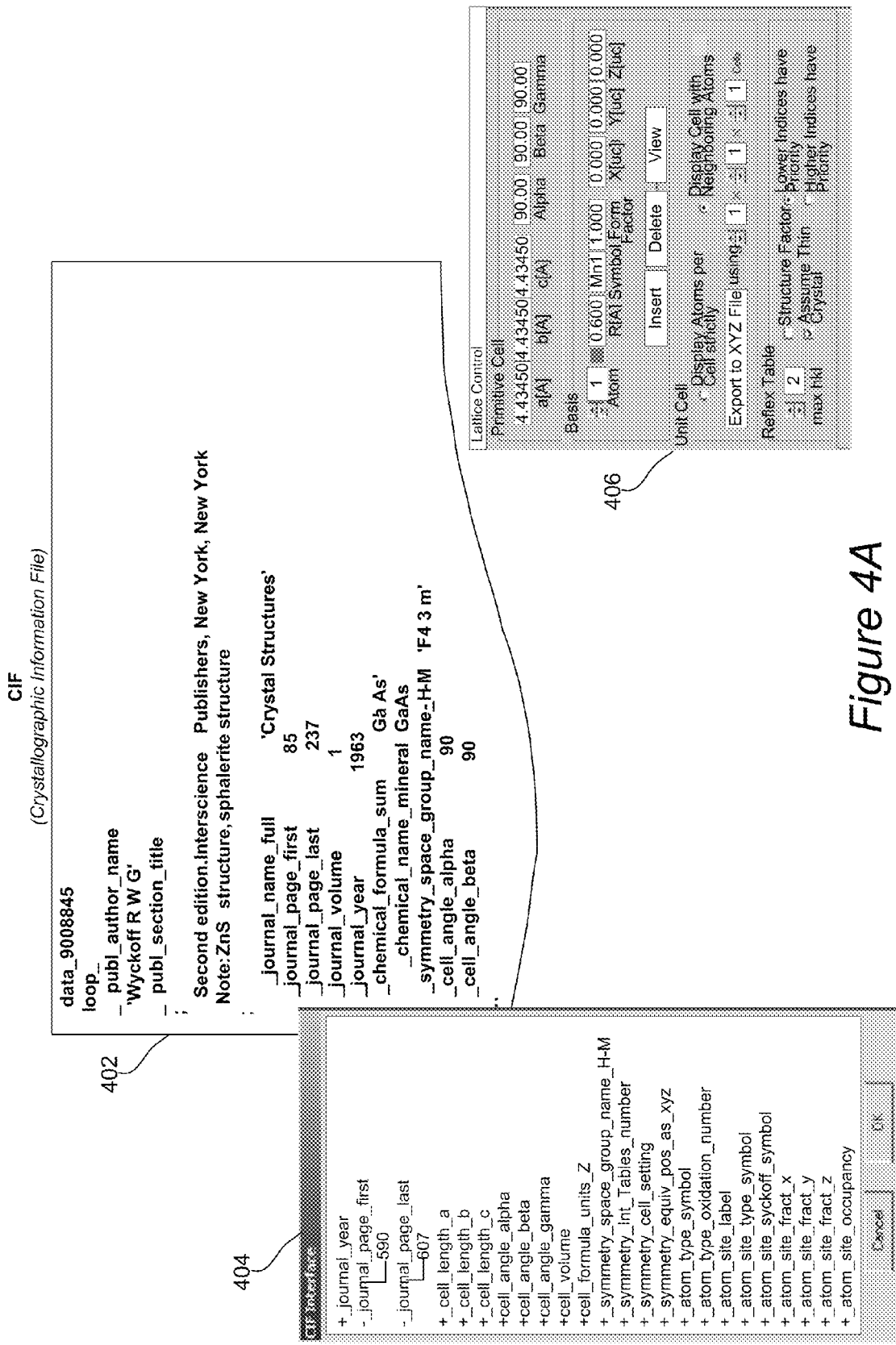
FIG. 4A includes example user interface mechanisms for a user to enter crystal parameters in accordance with a specific implementation of the present invention.

FIG. 3 is a flow chart illustrating an alignment procedure 300 in accordance with one embodiment of the present invention. Initially, crystal parameters may be received (as input to the alignment process) in operation 302. FIG. 4A includes example user interface mechanisms for a user to enter crystal parameters in accordance with a specific implementation of the present invention. As shown, a user may select a crystallographic information file (CIF) via CIF interface 404, for example, via a pull down "file→open" command. A CIF generally contains crystal parameters (as well as other data) in a standardized format. An example CIF for GaAs 402 is illustrated. By using CIF data, a user can easily switch between different crystal types by selecting different CIF's.

CIF information may be obtained from any suitable source. For example, numerous crystals are described in numerous CIF databases, which are accessible through various computer networks (e.g., via the Web). Example CIF databases include Crystallographic Open Database, American Mineralogist Crystal Structure database, the Cambridge Structural Database, NIST (National Institute of Standards and Technology of Gaithersburg, Md.), MYNCRYST, etc. A CIF may also be constructed or modified using various crystal kit CIF interfaces, such as EnCIFer available from The Cambridge Crystallographic Data Centre of Cambridge, England and CIFEdit available from the International Union of Crystallography of Chester, England.

The selected CIF may be automatically parsed so as to extract crystal parameters that will be used for various alignment techniques described further herein. As shown, after CIF selection, the CIF interface may be automatically populated with crystal parameters shown in a collapsed fashion. Each crystal parameter may be selected by the user to then expand the selected item to view the selected parameter value.

After user input for crystal parameters (e.g., a selected CIF) is received, a lattice control interface 406 may also be presented to the user. The lattice control window 406 may allow the user to adjust certain crystal parameters, such as cell lengths, cell angles, base atom types and positions within the crystal unit, etc. The lattice control window 406 may also allow the user to select various options such as a structure factor calculation which modulates the intensity of the simulated diffraction spots according to kinematic diffraction theory and the definition of a Burgers vector which corresponds to a crystal defect, to modulate the color of the simulated diffraction spots in order to identify the visibility of the designated crystal defect in the case the spot is used for dark-field imaging.

Figure 4B:
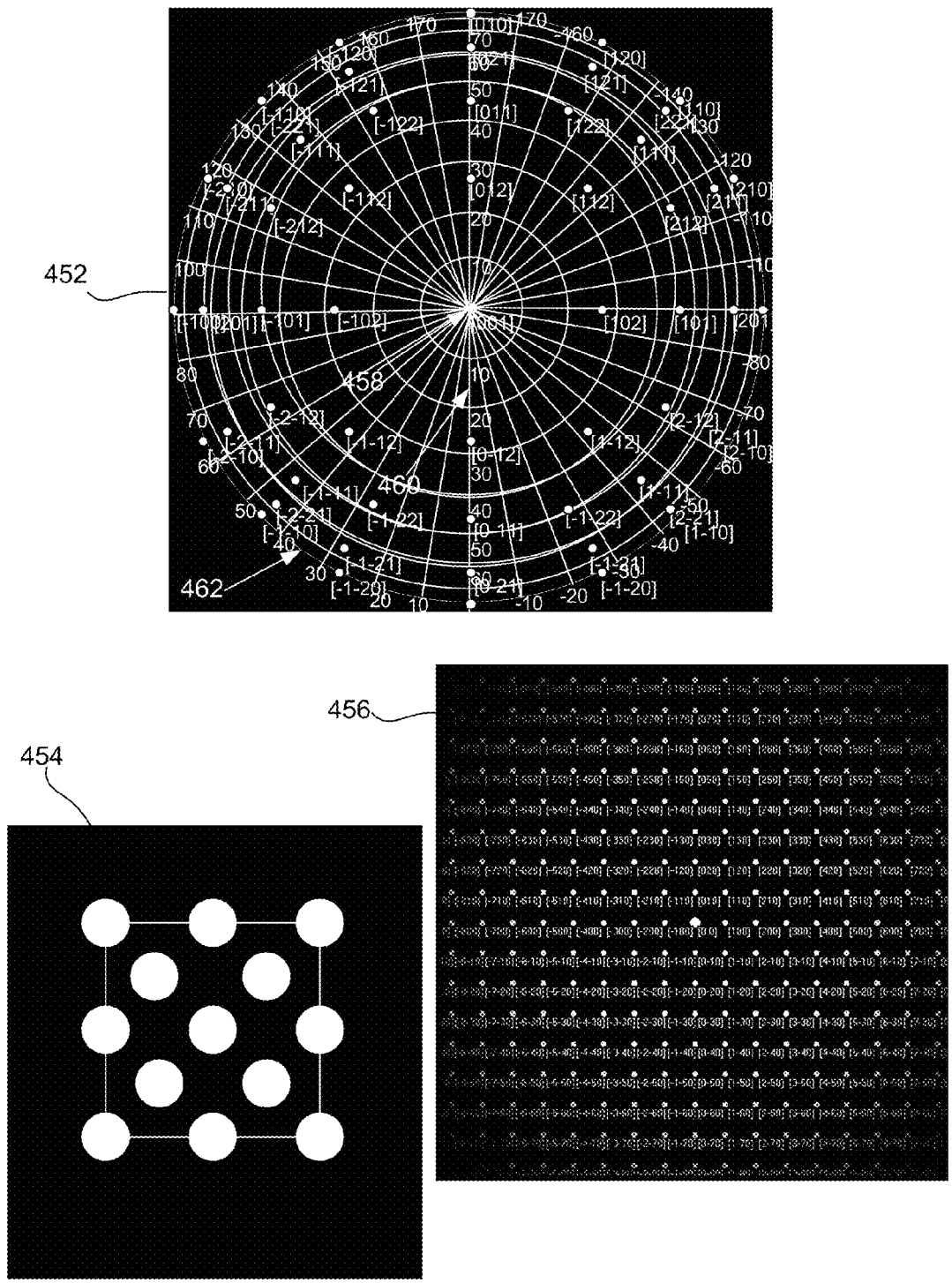
FIG. 4B illustrates various viewing interfaces in accordance with one embodiment of the present invention.

The user interface may also include various viewing interfaces for presenting different aspects of the crystal to aid in alignment of such crystal. FIG. 4B illustrates various viewing interfaces in accordance with one embodiment of the present invention. Referring to the illustrated example of FIG. 3 and FIG. 4, an interactive control sphere 452 for moving the stage and crystal sample, as well as showing the relationship between the stage and crystal positions or orientations, may be presented in the display interface (associated with the TEM system) in operation 304. The control sphere 452 generally contains stage coordinates and crystal pole coordinates (e.g., in Miller indices form) although these different coordinate systems are not aligned with each other after initially loading the sample. For example, the sample may be cut and loaded to initially view the [001] plane, but the crystal [001] plane is typically misaligned with respect to the sample surface (e.g., as shown in FIG. 2B).

On the control sphere 452 tilt ($\alpha$) angles for the stage are shown along circumference line 460 and rotation ($\gamma$) angles for the stage are shown along the circumference line 462 (which appears as an outside ring along the two dimensional view of the sphere). If a double-tilt stage was utilized, a second tilt angle (and coordinates) would be shown on the sphere, corresponding to the second tilt angles positions of the double-tilt stage. The control sphere is movable by the user via any suitable input mechanisms (e.g., a trackball or mouse) so that the stage and crystal can be moved. For instance, at least theoretically, the sphere may be moved through each of these tilt and rotation angles by 0 through +180 degrees and 0 through −180 degrees. However, if the stage has movement limits (e.g., can only achieve 77 degrees of $\alpha$ angle), the sphere may also show the limits for these off-limit angles, for example, in a red color (not shown). This approach is useful for determining if an anticipated pole is in reach after the coordinate systems have been aligned, in contrast to a trial-and-error technique. It is noted that although the control sphere shows the pole [001] as corresponding to viewing $\alpha$ angle of 0 degrees, the pole is typically located at a different a stage angle. For instance, although the crystal may be cut and loaded into the stage so as to present pole [001], there may be misalignment between the stage and the actual crystal planes as shown in the sphere. Techniques for synchronizing the crystal coordinates to the stage coordinates are described further herein.

A simulated cell view 454 and simulated diffraction pattern 456 may also be presented in the display interface in operation 306. The simulated diffraction pattern may be used to perform fingerprinting. The movement of the simulated cell view 454 and diffraction pattern 456 may be coupled with the movement of the control sphere 452. That is, as the user moves the control sphere and crystal, the simulated cell view 454 and diffraction pattern 456 also moves (although are initially misaligned with the stage coordinates).

The simulated cell view and diffraction pattern (e.g., diffractogram or Kikuchi lines) may be simulated by any suitable manner. In general, the crystal parameters, e.g., which are input by a user, may be used to calculate a cell view comprised of cell positions and a diffraction pattern comprising diffraction points, as well as pole positions. This calculation or determination process may be carried out by any suitable software package for simulating crystal views and/or diffraction patterns, such as CrystalKit available from Total Resolution LLC of Berkeley, Calif.

So as to synchronize all of these available crystal and stage views, the user may be presented with various options for automatic alignment. Returning to the illustrated process, an interactive mechanism for automatically calculating the current tilt axis or pole orientation is presented in operation 308. The automatic tilt axis or pole position calculation is generally based on the simulated model and user selection of diffraction points of the actual diffraction pattern obtained from the imaged crystal. In one example, the user may select a crossover point on the Kikuchi Line pattern (obtained from the imaged crystal) for geometrically determining a center pole position. In another example, the user selects a center or diffraction points for two Laue zones of a diffraction pattern obtained from imaging the crystal. The user also identifies the current pole (e.g., via Miller indices) that is being viewed (although misaligned).

Figure 5A:
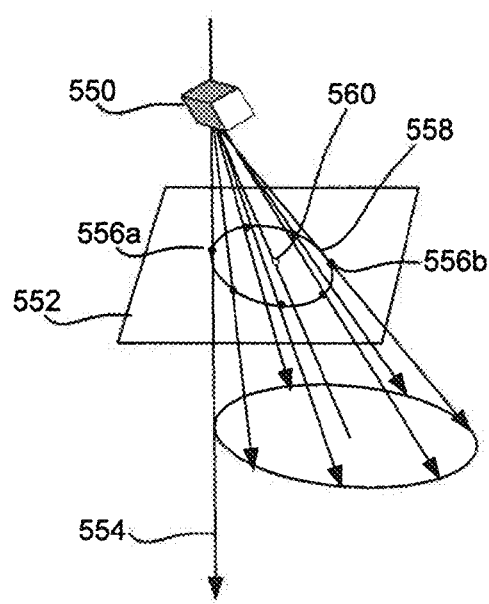
FIG. 5A illustrates a Laue zone comprised of diffraction points at a screen when a crystal is tilted with respect a particular alpha or viewing axis.

FIG. 5A illustrates a Laue zone 558 comprised of diffraction points (e.g., 556a and 556b) at a screen 552 when a crystal 550 is tilted with respect a particular alpha or viewing axis 554. In general, each diffraction point in the Laue zone corresponds to a specific plane orientation, and the center 560 of such Laue zone corresponds to a highly symmetric pole which usually has a low sum of Miller indices. Each Laue zone can be mapped to an intersection of an Ewald sphere, which is typically circular although the Laue zone as it intersects with the screen may appear elliptical.

Figure 5B:
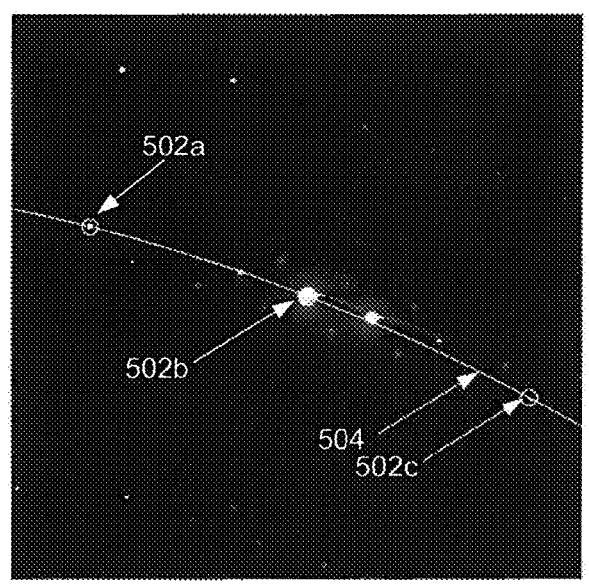
FIG. 5B shows a mechanism for selecting diffraction points within a Laue zone in accordance with one embodiment of the present invention.

The center 560 of such zone may be calculated when the user selects three or more displayed diffraction points in the Laue zone of a user identified pole. FIG. 5B shows a mechanism for selecting diffraction points within a Laue zone in accordance with one embodiment of the present invention. The tilt angle is moved (e.g., by the user) until a Laue zone is presented clearly in the diffraction pattern that is obtained from the crystal and displayed to the user. The user may select 3 non-collinear points along the displayed Laue zone. For example, diffraction points 502a, 502b, and 502c in Laue zone 504 are displayed and selected by the user. Selection may be shown in any suitable manner, for example, by presenting circles around the selected diffraction points. The user then tilts to another tilt angle and repeats the selection of 3 points in either the same or another Laue zone. Alternatively, the user may simple select the centers of two or more Laue zones (if visible).

When the crystal is moved to another alpha tilt angle and Laue zone, the center of this other Laue zone coincides with the previous Laue zone center position if the tilt angle is not too large (the close Laue zones are concentric around a low-index pole). Based on the known tilt angle change, displacement of the identified center, and knowledge of the camera length calibration, the alpha tilt axis orientation and the currently identified pole's position with respect to such current stage position may be automatically calculated. In effect, the simulated model is lined up with the reality of the imaged crystal. A tilt offset between the current stage and the crystal positions (or a tilt angle relationship between such different coordinate systems) may also be automatically determined based on such simple user selections of diffraction points. The camera length can be determined with the diffraction pattern overlay, by matching the overlay to the picture acquired from the microscope. Similar techniques may be applied to determining a pole's position for a double tilt stage by performing the similar diffraction point selections for two alpha tilt angles.

Once the current pole position (e.g., tilt angle) is known, an interactive mechanism for adjusting rotation angle for the selected pole orientation may be presented in the display interface so as to facilitate alignment of the simulated diffraction pattern (or Kikuchi lines) with the diffraction pattern (or Kikuchi lines) obtained from crystal sample in operation 310. In sum, the actual diffraction image is aligned to the diffraction model to get an azimuth angle. Even though the pole position may have been found based on the Laue zone center displacement technique, there is an ambiguity as the sample can be rotated around the pole.

Figure 6A:
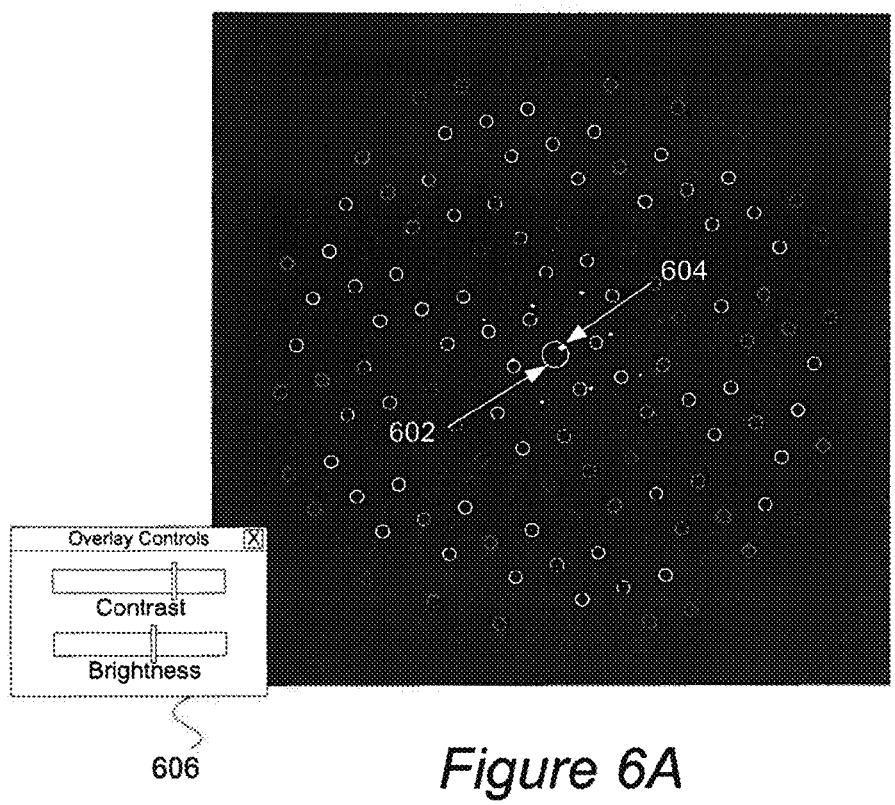
FIG. 6A represents an image that includes a simulated diffraction pattern overlaid with a misaligned diffraction pattern obtained from a particular crystal in accordance with one embodiment of the present invention.
Figure 6B:
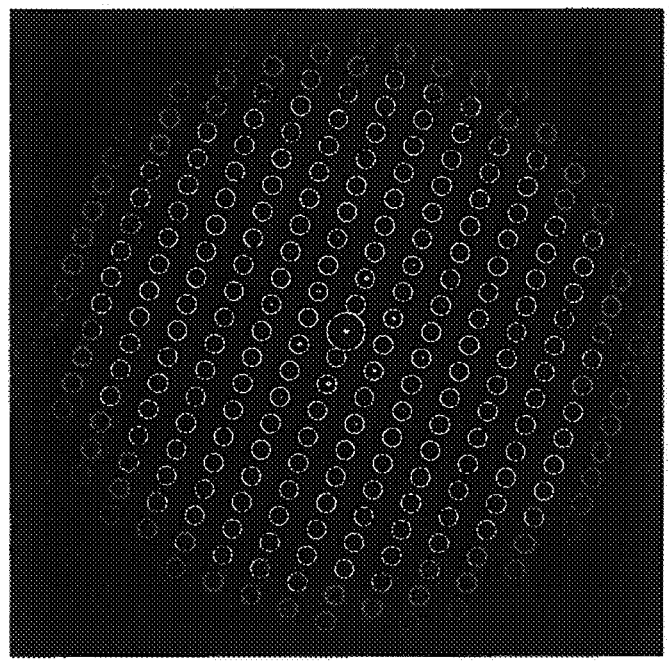
FIG. 6B represents an image that includes a simulated diffraction pattern overlaid with an aligned diffraction pattern obtained from a particular crystal in accordance with one embodiment of the present invention.

FIG. 6A represents an image that includes a simulated diffraction pattern overlaid with a misaligned diffraction pattern obtained from a particular crystal in accordance with one embodiment of the present invention. As shown, the simulated diffraction pattern is represented by open circles (e.g., center simulated diffraction point 602) and the imaged diffraction points are represented by dots (e.g., center diffraction point 604). The user can select an option to align the azimuth angle (e.g., via a pull down menu). After the user selects the azimuth angle alignment option, the imaged diffraction pattern may be moved relative to the simulated diffraction points by adjusting the azimuth angle (and camera angle). FIG. 6B represents an image that includes a simulated diffraction pattern overlaid with an aligned diffraction pattern obtained from a particular crystal in accordance with one embodiment of the present invention.

Figure 7:
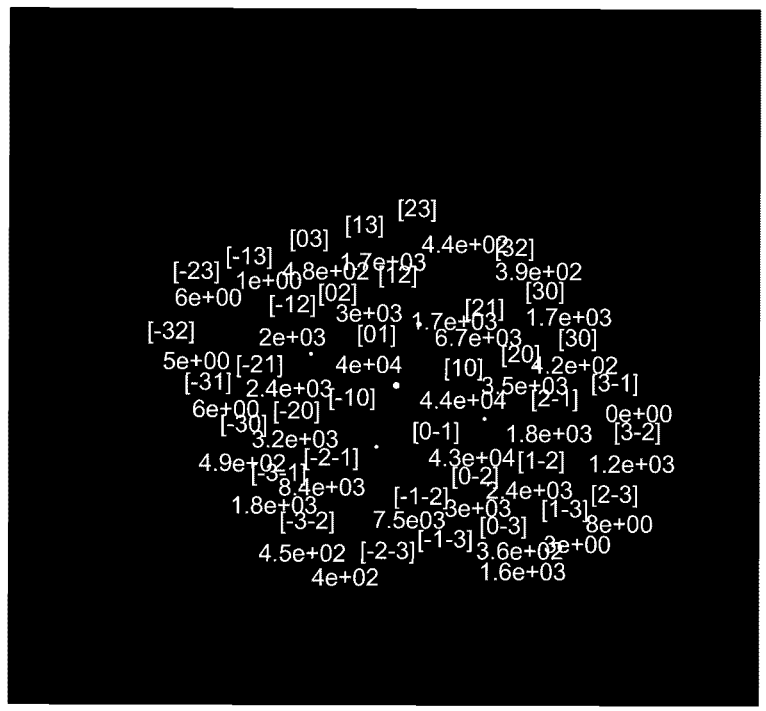
FIG. 7 illustrates the diffraction points from a crystal after a fine tuning option has been selected in accordance with one embodiment.

A fine tuning process may also be implemented. As shown in the illustrated embodiment, an interactive mechanism for fine tuning alignment between the stage position and crystal coordinates using a center of gravity (or mass) process for the diffraction pattern from the crystal may be presented in the display interface in operation 312. FIG. 7 illustrates the diffraction points from the crystal after the fine tuning option has been selected in accordance with one embodiment. The diffraction points will tend to have varying intensity levels, which can be seen in the display interface. The user may then select the center of the diffraction patterns, as well as two non-colinear points. Based on these selections, a center of gravity may then be calculated to determine the amount that the stage angles need to be further adjusted for the adjustment of the current pole position (if any). Alternatively, the determination of a center of gravity could be based on an automatic detection of the intensity peaks or points, rather than a manual selection of a few diffraction points.

The fine tuning process may not only be used for initial adjustments, but may also be used for a final approach to the crystal. That is, the fine tuner can be used to predict the last tiny bit of tilt adjustment and help to go to the final approach. This approach rids the need of an operator having to tilt in very accurately at the final approach so as to account for microscope backlash.

After the alignment processes are performed, a more accurately aligned interactive control sphere (e.g., for moving stage and crystal sample, as well as showing relationship between stage and crystal orientations) may then be presented in the display interface in operation 314. During the alignment process, offsets may have been calculated between the different coordinate systems (e.g., microscope display, sample, stage, crystal) so that the stage can now be automatically moved to a particular crystal position via simple coordinate system transformations. The user may select or enter a specific pole position (e.g., Miller index), and the control sphere and stage are the automatically moved to the selected pole position so as to optimally view such pole position. Additionally, linearization tables may be calculated that allow matching of the ideal model scales to any real stage scales, which may be non-linear.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A method of generating an image or diffraction patterns from a crystal sample with a microscope having a beam generator for directing an incident beam towards a crystal sample, a stage for holding and moving the crystal sample, a detector for detecting beams that are scattered from the sample in response to the incident beam, and an image generator for generating an image or diffraction patterns of the crystal sample from the scattered beams, the method comprising:

receiving a plurality of crystal parameters that describe a plurality of properties of the crystal sample; and in a display associated with the microscope, presenting an interactive control sphere based at least in part on the received crystal parameters and having a same rotational constraints as the stage and that is rotatable by a user to different sphere orientations, wherein the control sphere includes a plurality of stage coordinates that correspond to a plurality of positions of the stage and a plurality of crystallographic coordinates that correspond to a plurality of crystallographic pole positions of the crystal sample, wherein movement of the sphere causes movement of the stage, wherein the stage coordinates move in conjunction with the crystallographic coordinates so as to show a relationship between stage positions and the crystallographic pole positions.

2. The method of claim 1, wherein the received crystal parameters are received in the form of a crystallographic information file (CIF).

3. The method of claim 1, wherein the stage is a tilt-rotation type stage, and wherein the stage coordinates include coordinates for a plurality of tilt angles and a plurality of rotation angles of the stage.

4. The method of claim 1, wherein the stage is a double tilt type stage, and wherein the stage coordinates include coordinates for a plurality of two tilt angles and a plurality of rotation angles of the stage.

5. The method of claim 1, wherein the stage and pole coordinates of the control sphere are misaligned immediately after loading the sample onto the stage.

6. The method of claim 5, further comprising:
automatically synchronizing the stage and crystallographic coordinates of the control sphere based on a user alignment process; and
after synchronizing the stage and crystallographic coordinates of the control sphere and when a specific pole position is selected, automatically moving the stage, along with the presented control sphere, to the selected pole position.

7. The method of claim 6, wherein the selected pole position is selected by a user entering Miller indices for the selected pole or rotating the control sphere to a particular crystallographic coordinate that corresponds to the entered Miller indices.

8. The method of claim 7, wherein presenting the interactive sphere is also based on simulating a simulated diffraction pattern based at least, in part, on the received crystal parameters, and wherein the user alignment process comprises:
in a display associated with the microscope, presenting an actual diffraction pattern obtained from imaging the crystal sample;
receiving selection of a center or a plurality of diffraction points of the actual diffraction pattern for geometrically determining the center; and
automatically determining a tilt angle relationship between the stage and pole positions based on the selection of the center or the plurality of diffraction points of the actual diffraction pattern.

9. The method of claim 8, wherein selection comprises selection of the center or selection of three non-colinear diffraction points for each of either two Laue zones or a same Laue zone of the actual diffraction pattern acquired at two different tilt angles.

10. The method of claim 8, wherein the actual diffraction pattern is in the form of a Kikuchi line pattern, and user selection comprises selection of the center or selection of a plurality of crossover points of the Kikuchi line pattern.

11. The method of claim 8, wherein the user alignment process further comprises:
in the display, presenting an overlay of the simulated diffraction pattern and the actual diffraction pattern;
receiving an adjustment of a rotation position of the crystallographic coordinates with respect to the actual diffraction pattern, wherein the adjustment is accomplished by rotating the simulated diffraction pattern with respect to the actual diffraction pattern to thereby cause alignment of a plurality of crystallographic model coordinates with a plurality of actual crystallographic sample coordinates;
automatically determining a rotation angle relationship between the stage and pole positions based on the received adjustment;
in the display, presenting the actual diffraction pattern and its plurality of different intensity values of diffraction points;
receiving a selection of a center and a plurality of non-colinear points of the actual diffraction pattern; and
automatically adjusting the determined rotation relationship based on a center of mass calculation of the different intensity values with respect to the center of the actual diffraction pattern and non-colinear points so as to align the stage and pole positions of the control sphere to thereby accurately correspond with the stage and pole positions of the crystal sample.

12. A microscope configured to generate an image or diffraction patterns from a crystal sample, comprising:
a beam generator configured to direct an incident beam to the crystal sample;
a stage configured to hold and to move the crystal sample;
a detector configured to detect scattered beams that are scattered from the crystal sample from the incident beam;
an image generator configured to generate an image or diffraction patterns of the crystal sample from the scattered beams; and
a controller configured to perform the following operations:
receive crystal parameters that describe properties of the crystal sample; and
in a display associated with the microscope, present a control sphere, based at least in part on the crystal parameters, the control sphere having a same rotational constraints as the stage and being rotatable to different sphere orientations, wherein the control sphere includes stage coordinates that correspond to positions of the stage and crystallographic coordinates that correspond to crystallographic pole positions of the crystal sample, wherein movement of the sphere causes movement of the stage, wherein the stage coordinates move in conjunction with the crystallographic coordinates so as to show a relationship between stage positions and the crystallographic pole positions.

13. The microscope of claim 12, wherein the crystal parameters are received in the form of a crystallographic information file (CIF).

14. The microscope of claim 12, wherein the stage is a tilt-rotation type stage, and wherein the stage coordinates include coordinates for tilt angles and rotation angles of the stage.

15. The microscope of claim 12, wherein the stage is a double tilt type stage, and wherein the stage coordinates include coordinates for a tilt angles and rotation angles of the stage.

16. The microscope of claim 12, wherein the stage and the crystallographic coordinates of the control sphere are misaligned after loading the crystal sample onto the stage, and wherein the controller is further configured to:
synchronize the stage and the crystallographic coordinates of the control sphere based on a user alignment process; and
when a specific pole position is received, moving the stage, along with the control sphere, to the specific pole position.

17. The microscope of claim 16, wherein the specific pole position is received in the form of Miller indices for the specific pole position or by the rotation of the control sphere to a particular crystallographic coordinate.

18. The microscope of claim 17, wherein the control sphere is further based on simulating a simulated diffraction pattern based on the crystal parameters, and wherein the user alignment process comprises:
in a display associated with the microscope, presenting an actual diffraction pattern obtained from the crystal sample;
receiving a selection of a center or a plurality of diffraction points of the actual diffraction pattern for geometrically determining the center; and
determining a tilt angle relationship between the stage and pole positions based on the selection of the center or the plurality of diffraction points of the actual diffraction pattern.

19. The microscope of claim 18, wherein the selection comprises the center or three non-colinear diffraction points for each of either two Laue zones or a same Laue zone of the actual diffraction pattern acquired at two different tilt angles.

20. The microscope of claim 18, wherein the actual diffraction pattern is in the form of a Kikuchi line pattern, and wherein the selection comprises selection of crossover points of the Kikuchi line pattern.

21. The microscope of claim 18, wherein the user alignment process further comprises:
in the display, presenting an overlay of the simulated diffraction pattern and the actual diffraction pattern;
receiving an adjustment of a rotation position of the crystallographic coordinates with respect to the actual diffraction pattern, wherein the adjustment is accomplished by rotating the simulated diffraction pattern with respect to the actual diffraction pattern to cause alignment of crystallographic model coordinates with actual crystallographic sample coordinates;
determining a rotation angle relationship between the stage and pole positions based on the received adjustment;
in the display, presenting the actual diffraction pattern and its different intensity values of diffraction points;
receiving a selection of a center and non-colinear points of the actual diffraction pattern; and
adjusting the determined rotation relationship based on a center of mass calculation of the different intensity values with respect to the center of the actual diffraction pattern and non-colinear points so as to align the stage and pole positions of the control sphere to correspond with the stage and pole positions of the crystal sample.

22. The microscope of claim 12, wherein the incident beam is an electron beam, and wherein the microscope is a transmission electron (TEM) microscope.

23. At least one computer readable storage medium having computer program instructions stored thereon that are arranged for generating an image or diffraction patterns of a sample with a microscope having a beam generator for directing an incident beam towards a crystal sample, a stage for holding and moving the crystal sample, a detector for detecting beams that are scattered from the crystal sample in response to the incident beam, and an image generator for generating an image or diffraction patterns of the crystal sample from the scattered beams, wherein the program instructions are arranged to perform the following operations:
receiving a plurality of crystal parameters that describe a plurality of properties of the crystal sample; and
in a display associated with the microscope, presenting an interactive control sphere based at least in part on the received crystal parameters and having a same rotational constraints as the stage and that is rotatable by a user to different sphere orientations, wherein the control sphere includes a plurality of stage coordinates that correspond to a plurality of positions of the stage and a plurality of crystallographic coordinates that correspond to a plurality of crystallographic pole positions of the crystal sample, wherein movement of the sphere causes movement of the stage, wherein the stage coordinates move in conjunction with the crystallographic coordinates so as to show a relationship between stage positions and the crystallographic pole positions.

24. The at least one computer readable storage medium of claim 23, wherein the program instructions are further arranged to perform the following operations:
automatically synchronizing the stage and crystallographic coordinates of the control sphere based on a user alignment process; and
after synchronizing the stage and crystallographic coordinates of the control sphere and when a specific pole position is selected, automatically moving the stage, along with the presented control sphere, to the selected pole position.

25. The at least one computer readable storage medium of claim 24, wherein the selected pole position is selected by a user entering Miller indices for the selected pole or rotating the control sphere to a particular crystallographic coordinate that corresponds to the entered Miller indices.

26. The at least one computer readable storage medium of claim 25, wherein presenting the interactive sphere is also based on simulating a simulated diffraction pattern based at least, in part, on the received crystal parameters, and wherein the user alignment process comprises:
in a display associated with the microscope, presenting an actual diffraction pattern obtained from imaging the crystal sample;
receiving selection of a center or a plurality of diffraction points of the actual diffraction pattern for geometrically determining the center; and
automatically determining a tilt angle relationship between the stage and pole positions based on the selection of the center or the plurality of diffraction points of the actual diffraction pattern.

27. The at least one computer readable storage medium of claim 26, wherein selection comprises selection of the center or selection of three non-colinear diffraction points for each of either two Laue zones or a same Laue zone of the actual diffraction pattern acquired at two different tilt angles.

28. The at least one computer readable storage medium of claim 26, wherein the user alignment process further comprises:
in the display, presenting an overlay of the simulated diffraction pattern and the actual diffraction pattern;
receiving an adjustment of a rotation position of the crystallographic coordinates with respect to the actual diffraction pattern, wherein the adjustment is accomplished by rotating the simulated diffraction pattern with respect to the actual diffraction pattern to thereby cause alignment of a plurality of crystallographic model coordinates with a plurality of actual crystallographic sample coordinates;
automatically determining a rotation angle relationship between the stage and pole positions based on the received adjustment;
in the display, presenting the actual diffraction pattern and its plurality of different intensity values of diffraction points;
receiving a selection of a center and a plurality of non-colinear points of the actual diffraction pattern; and
automatically adjusting the determined rotation relationship based on a center of mass calculation of the different intensity values with respect to the center of the actual diffraction pattern and non-colinear points so as to align the stage and pole positions of the control sphere to thereby accurately correspond with the stage and pole positions of the crystal.

* * * * *